United States Patent
Higuchi et al.

(10) Patent No.: US 6,956,602 B2
(45) Date of Patent: Oct. 18, 2005

(54) ELECTRONIC ENDOSCOPE FOR HIGHLIGHTING BLOOD VESSEL

(75) Inventors: Mitsuru Higuchi, Saitama (JP); Daisuke Ayame, Saitama (JP); Kazunori Abe, Saitama (JP); Shinji Takeuchi, Saitama (JP); Keiichi Negishi, Yokohama (JP)

(73) Assignee: Fujinon Corporation, Saitama (JP)

( * ) Notice: Subject to any disclaimer, the term of this patent is extended or adjusted under 35 U.S.C. 154(b) by 348 days.

(21) Appl. No.: 10/255,079

(22) Filed: Sep. 26, 2002

(65) Prior Publication Data

US 2003/0071894 A1   Apr. 17, 2003

(30) Foreign Application Priority Data

Sep. 27, 2001 (JP) ............................ 2001-295272
Sep. 27, 2001 (JP) ............................ 2001-295273
Jan. 30, 2002 (JP) ............................ 2002-021076

(51) Int. Cl.[7] ............................................ H04N 7/18
(52) U.S. Cl. ............................................. 348/65; 348/68
(58) Field of Search ............. 348/65–76; 600/100–125

(56) References Cited

U.S. PATENT DOCUMENTS

2003/0176768 A1 * 9/2003 Gono et al. ............... 600/109

* cited by examiner

Primary Examiner—Andy Rao
(74) Attorney, Agent, or Firm—Snider & Associates; Ronald R. Snider (57) ABSTRACT

The apparatus according to the present invention includes a level adjusting circuit that increases a gain of a G (or B) signal output from a color conversion circuit, a binarization circuit that forms a binarized image from this G signal and an edge detection circuit that extracts blood vessel position signals through edge detection based on this binarized signal. Then, the apparatus extracts RGB color signals making up a blood vessel image by using the above-described blood vessel position signals, increases the gains of these blood vessel color signals and then adds the blood vessel color signals to the color signals of an original image. This allows blood vessels to be displayed in high contrast to mucous membranes, etc. Furthermore, the apparatus can also amplify the R signal and B signal by using a signal obtained by differentiating the above-described G signal as a gain signal to highlight blood vessels.

9 Claims, 11 Drawing Sheets

FIG. 1

FIG. 2A
LEVEL ADJUSTMENT

FIG. 2B
BINARIZATION

FIG. 2C
EDGE DETECTION

FIG. 2D
ADDITION OUTPUT

FIG. 6A
AMPLIFIER OUTPUT

FIG. 6B
ADDITION OUTPUT

FIG. 7

FIG. 8A
G SIGNAL

FIG. 8B
LEVEL (La)

FIG. 8C
DIFFERENTIAL
SIGNAL

FIG. 9A
R SIGNAL

FIG. 9B
B SIGNAL

FIG. 10A
R SIGNAL

FIG. 10B
B SIGNAL

FIG. 10C
G SIGNAL

FIG. 10D
AFTER COMBINATION

ELECTRONIC ENDOSCOPE FOR HIGHLIGHTING BLOOD VESSEL

BACKGROUND OF THE INVENTION

This application claims the priority of Japanese Patent Applications Nos. 2001-295272 and 2001-295273 filed on Sep. 27, 2001 and No. 2002-21076 filed on Jan. 30, 2002 which are incorporated herein by reference.

1. Field of the Invention

The present invention relates to an electronic endoscope, and more particularly, to image processing of an electronic endoscope capable of displaying details of capillary blood vessels, etc. inside a body of an examinee.

2. Description of the Related Art

An electronic endoscope irradiates an object under observation with illuminating light to capture an image thereof through an objective optical system, takes in the image using an image pickup element such as a CCD (Charge Coupled Device) and displays this object image on a monitor, etc. In recent years, this type of electronic endoscope incorporates a power scaling mechanism in the above-described objective optical system and displays the optically magnified object image. This allows details of a focused area to be clearly observed with a magnified image shown on the monitor, etc.

SUMMARY OF THE INVENTION

Figure 13:
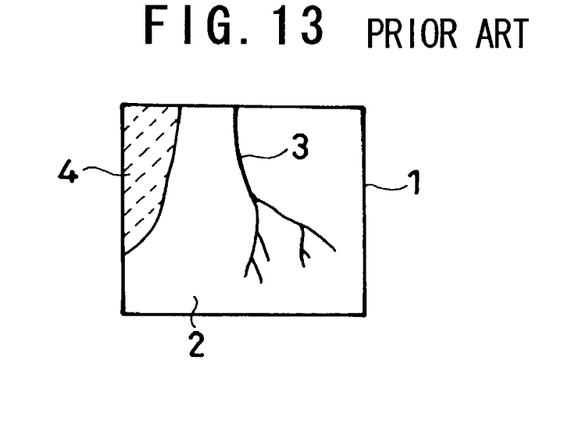
FIG. 13 shows a magnified image of an object taken and displayed by an electronic endoscope.

By the way, image pickup targets of the electronic endoscope are often objects inside a living body such as digestive organs, and as shown in FIG. 13, a magnified object image 1 (displayed on a monitor, etc.) includes a blood vessel (capillary blood vessel) 3 in a mucous membrane 2 and a blood circulation state and a concentration situation of this blood vessel (blood) 3 constitute important observation targets in making a diagnosis of a focus or identifying cancerous tissue, etc. On the other hand, since the interior of the living body has pink or reddish coloring, making a distinction between the blood vessel 3 and other tissue such as the mucous membrane 2 tends to become difficult. Thus, if the blood vessel 3 and the mucous membrane 2 could be displayed in sharp contrast to each other, it will be possible to provide information useful for observation and diagnosis of the living body. Reference numeral 4 denotes a dark area such as a groove.

The present invention has been achieved in view of the above-described problems and it is an object of the present invention to provide an electronic endoscope capable of clearly displaying an image of blood vessels in sharp contrast to other tissue such as mucous membranes.

To attain the above object, an electronic endoscope according to a first aspect of the present invention is characterized by including a color signal formation circuit that forms a predetermined color signal based on a signal obtained by an image pickup element, a binarization circuit that is fed color signals other than a red signal output from this color signal formation circuit and generates binarized image signals, an edge detection circuit that is fed the binarized signals output from this binarization circuit and detects/decides blood vessel positions in the image and a chroma adjusting circuit that adjusts chroma of the blood vessel image based on the blood vessel position signals output from this edge detection circuit and the above-described color signals. The above-described color signal formation circuit can form red, green and blue color signals and the above-described binarization circuit can form a binarized image using a green signal or blue signal.

The first aspect of the present invention forms color signals of R (red), G (green) and B (blue) using the color signal formation circuit and forms a binarized signal, that is, a white or black signal, using, for example, the G signal (or B signal). Since the binarized signal made up of this G signal does not include red color, blood vessels exist in the black signal area and mucous membranes exist in the white signal area. That is, this invention is designed to detect the existence of blood vessels from image signals with colors other than red which is a principal color of blood vessels. Then, edge detection is performed on this binarized signal and areas where white and black vary drastically are extracted as blood vessel position signals and other large areas are removed. Then, the RGB signals making up the blood vessel image are extracted by the above-described blood vessel position signals and these signals are amplified (with chroma increased) and then added to the RGB signals of the original image. As a result, even if a blood vessel exists in a mucous membrane, the blood vessel is displayed with sharp contrast.

A second aspect of the present invention is characterized by including, in addition to the above-described color signal formation circuit, above-described binarization circuit and above-described edge detection circuit, a blood vessel re-detection circuit that re-detects blood vessel position signals output from this edge detection circuit using a clock signal which is slower than an image processing clock signal and a chroma correction circuit that adjusts chroma of a blood vessel image based on the blood vessel position signals output from this blood vessel re-detection circuit and the above-described color signals.

The second aspect of the present invention redetects the blood vessel position signals obtained from the above-described edge detection circuit with a slow clock signal, which is obtained, for example, by dividing an image processing clock signal by 2 and thereby forms an image of a double-thick blood vessel. The chroma of this blood vessel image is increased by the chroma correction circuit and as a result, the double-thick blood vessel is displayed in the mucous membrane with high contrast.

In the above-described inventions, the chroma correction circuit increases the chroma of a blood vessel image by amplifying signals, but it is also possible to increase contrast between the blood vessel and mucous membrane by extracting signals other than the blood vessel position signals output from the above-described edge detection circuit or blood vessel re-detection circuit and reducing the chroma of images other than the image of this blood vessel.

A third aspect of the present invention is characterized by including a color signal formation circuit that forms a predetermined color signal based on the signal obtained by the image pickup signal, a differentiating circuit that differentiates a predetermined color signal other than the red signal obtained by this color signal formation circuit and forms a differential signal, a gain circuit that amplifies the differential signal output from this differentiating circuit and a blood vessel highlighting circuit that amplifies at least the red signal other than the above-described predetermined color signal based on the differential signal output from this gain circuit and highlights blood vessels. The above-described color signal formation circuit can form red, green and blue color signals, while the above-described differentiating circuit can apply differential processing to a green signal and the above-described blood vessel highlighting circuit can amplify the red and blue signals using the differential signal.

According to the third aspect of the present invention, the color signal formation circuit forms R, G and B color signals and the differentiating circuit performs differentiation processing on, for example, a G signal (or B signal). According to this G signal, blood vessels exist in a low-level signal area (black area) and mucous membranes exist in other areas. Blood vessel positions (existence) are extracted by detecting, through differentiation processing, locations which are changing drastically to a certain degree in this low-level area. That is, this invention detects blood vessel positions by applying differentiation processing to image signals with colors other than red which is a principal color of blood vessels.

Then, the differential signal obtained from the above-described differentiating circuit is amplified at a predetermined amplification factor, then supplied to the blood vessel highlighting circuit where the above-described R and B signals (or only R signal) are amplified by using this differential signal as a gain signal and an object image is formed by these R and B signals and the G signal which gives no differential signal. That is, an image is formed by the R and B signals which have been amplified according to the level of a drastic change of the above-described differential signal and the G signal immediately before the differentiating circuit, and as a result, a blood vessel in a mucous membrane is displayed in high contrast to each other.

BRIEF DESCRIPTION OF THE DRAWINGS

FIG. 2A to FIG. 2D are images formed in various circuits of the first embodiment.

FIG. 8A to FIG. 8C are obtained by the respective circuits of the fourth embodiment and FIG. 8A shows a G signal image.

FIG. 9A and FIG. 9B show outputs from the blood vessel highlighting circuit of the fourth embodiment and FIG. 8A shows an R signal of the horizontal line La and FIG. 8B shows a B signal;

FIG. 10A to FIG. 10D show images obtained by the respective circuits of the fourth embodiment and FIG. 10A shows an R signal image, FIG. 10B shows a B signal image, FIG. 10C shows a G signal image and FIG. 10D shows an RGB combined signal;

FIG. 12A to FIG. 12C show states of blood vessel highlighting processing of a G image of the fifth embodiment and FIG. 12A illustrates the G image, FIG. 12B illustrates an R image and FIG. 12C illustrates a final image.

DETAILED DESCRIPTION OF THE PREFERRED EMBODIMENTS

First Embodiment

Figure 1:
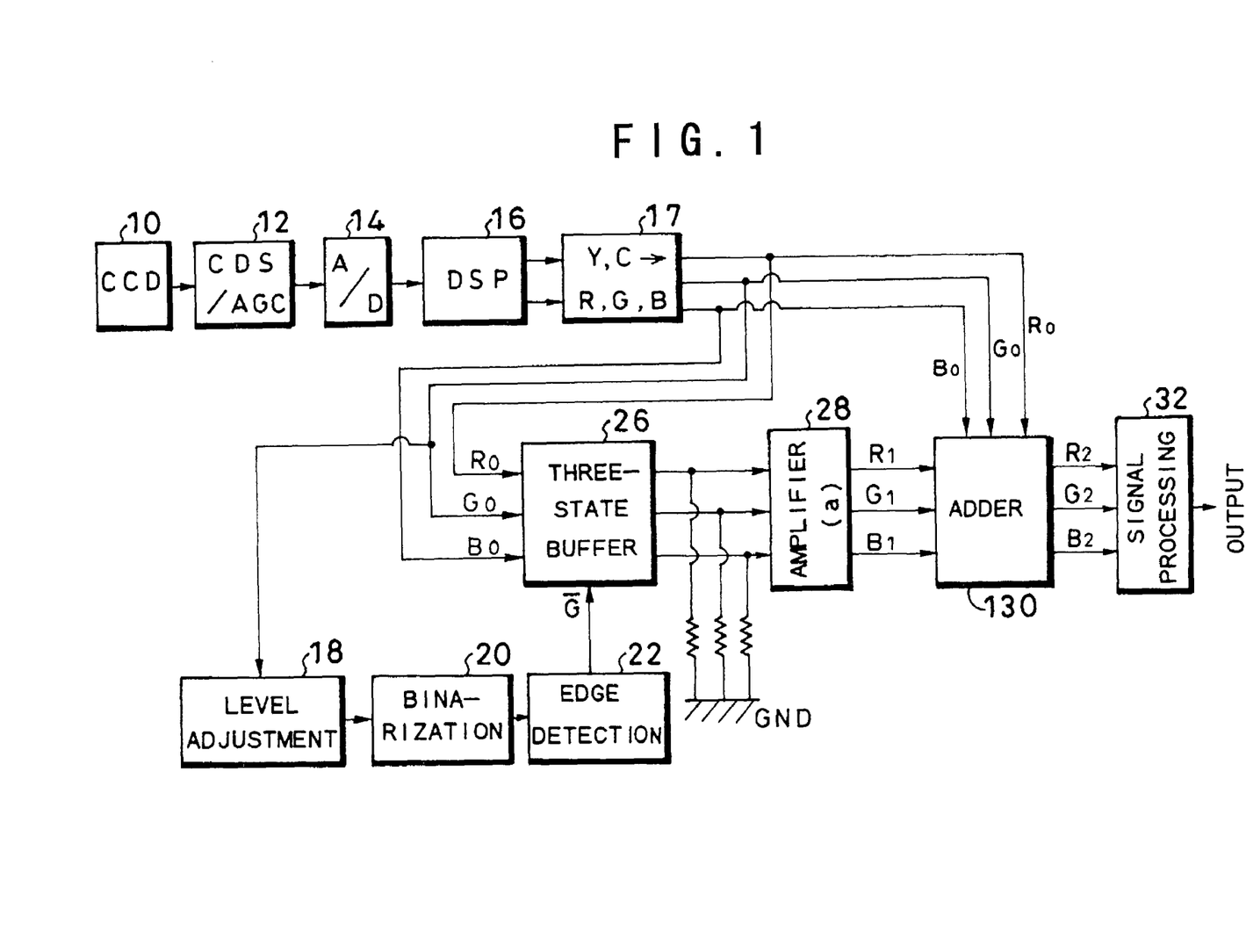
FIG. 1 is a block diagram showing a main configuration of an electronic endoscope according to a first embodiment of the present invention.

FIG. 1 shows a configuration of part of an electronic endoscope according to a first embodiment and this electronic endoscope is, for example, of a synchronous type and is provided with a scope, a processor unit, a light source unit, a monitor and a recorder, etc. In this FIG. 1, a CCD 10, an image pickup element, is provided at a tip of the scope and this CCD 10 captures an image of an object through color filters on a pixel-by-pixel basis (e.g., Mg (magenta), G (green), Cy (cyan) and Ye (yellow)). That is, when light from the above-described light source unit is irradiated from the tip of the scope onto the object through a light guide, the image of this object is taken by the CCD 10. Furthermore, if an objective optical system with a built-in power scaling movable lens is provided, in front of this CCD 10, it is possible to obtain a magnified image of the object by driving this power scaling lens.

The above-described CCD 10 is followed by a CDS (Correlated Double Sampling)/AGC (Automatic Gain Control) 12 and this CDS/AGC 12 applies correlated double sampling to an output signal of the CCD 10 and applies predetermined amplification processing as well. This CDS/AGC 12 is provided with a DSP (Digital Signal Processor) 16 via an A/D (analog/digital) converter 14.

This DSP 16 performs various types of processing such as white balance, gamma correction and forms a Y (brightness) signal and color difference (C) signals R (red)-Y and B (blue)-Y, and this DSP 16 is followed by a color conversion circuit 17 for converting the above-described Y signal and C signal to R, G, B signals. That is, the above-described DSP 16 in this embodiment forms Y signal, C signals of R-Y and B-Y by performing a color conversion operation from signals obtained via various color filters of Mg, G, Cy and Ye. By further performing a color conversion operation on these Y and C signals, R, G and B color signals are obtained. By the way, it is also possible to directly form RGB signals within the above-described DSP 16 instead of color difference signals.

Then, the first embodiment performs processing for identifying blood vessels using signals other than an R signal, that is, a G signal or B signal. For this purpose, this embodiment provides a level adjusting (gain increasing) circuit 18 that inputs the G signal output from the above-described color conversion circuit 17, adjusts the level of this signal and performs mean value matching for binarization, a binarization circuit 20 that converts the output signal of this level adjusting circuit 18 to a binarized signal and an edge detection circuit 22 that detects an area where the output signal of this binarization circuit 20 changes drastically (removing a low frequency component of the signal) and extracts a blood vessel position signal.

That is, the above-described level adjusting circuit 18 increases the gain by a predetermined amount so that the mean value of the G signal (or can also be values at other levels) matches the mean (intermediate) value of binarization. For example, in the case where signal levels are expressed with 256 digital values and when a signal level is greater than the mean value 128, the value is assumed to be "1" (white) and when the signal level is equal to or lower than this mean value 128, the value is assumed to be "0" (black), then the G signal is amplified so that the mean value of the G signal matches the mean value 128. Furthermore, the edge detection circuit 22 extracts (removes the area of the image signal whose frequency is low) the edge area where the above-described binarized signal changes drastically and thereby extracts blood vessel position information (information of positions at which blood vessels exist).

After the above-described color conversion circuit 17, there are a three-state buffer 26 that is fed color signals of $R_0$, $G_0$ and $B_0$ obtained here and also fed output signals from the above-described edge detection circuit 22 and an amplifier 28 and these circuits constitute a chroma correction circuit. That is, the above-described three-state buffer 26 extracts color signals corresponding to the respective blood vessel positions based on the blood vessel position signals (e.g., High signal) output from the edge detention circuit 22 and the above-described amplifier 28 amplifies the respective signals of $R_0$, $G_0$ and $B_0$ corresponding to this blood vessel position at a predetermined amplification factor.

The above-described amplifier 28 is followed by an adder 30 that adds up signals of $R_0$, $G_0$ and $B_0$ and signals $R_1$, $G_1$ and $B_1$ output from the amplifier 28 respectively and output signals $R_2$, $G_2$ and $B_2$, and this adder 130 is provided with a signal processing circuit 32 that performs various types of processing for monitor output.

The first embodiment has the configuration as described above and its operation will be explained with reference to FIG. 2A to FIG. 2D. First, when an image of an object irradiated with light emitted from the tip of the scope is taken by the CCD 10, the output signal of this CCD 10 is sampled and amplified by the CDS/AGC 12 and supplied as a digital signal to the DSP 16 via the A/D converter 14. As described above, this DSP 16 forms a Y signal and C (color difference) signals of R-Y and B-Y subjected to various types of image processing and the color conversion circuit 17 converts this Y signal and C signal to color signals $R_0$, $G_0$ and $B_0$ respectively. Then, these signals are supplied to the three-state buffer 26 and at the same time the $G_0$ signal of the three is input to the level adjusting circuit 18.

Figure 2A:
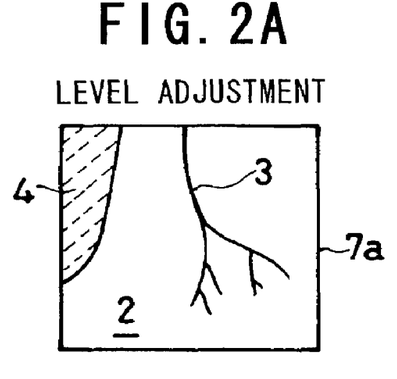
FIG. 2A shows an image after a level adjustment.
Figure 2B:
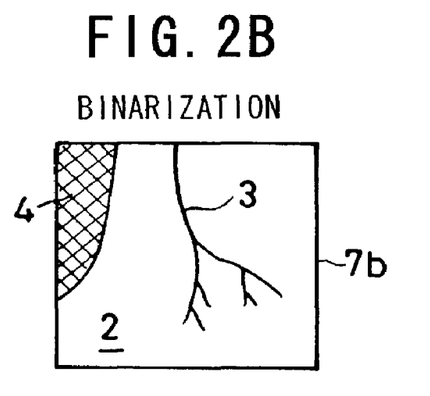
FIG. 2B shows a binarized image.

This level adjusting circuit 18 increases the gain of the $G_0$ signal by a predetermined amount and obtains an image 7a shown in FIG. 2A for an object shown in FIG. 13, for example. Here, with the image 1 in FIG. 13, the blood vessel 3 is expressed in red, while with the image 7a in FIG. 2A, the blood vessel color includes no green component, and therefore the blood vessel 3 is displayed in black. Then, when the level-adjusted G signal is supplied to the binarization circuit 20, the signal is replaced by two values; "0" when the level is 128 or below and "1" when the level is greater than 128. This state is shown in the image 7b in FIG. 2B and the mucous membrane 2 is expressed in white (1) and dark area 4 such as the blood vessel 3 and the groove is expressed in black (0).

Figure 2C:
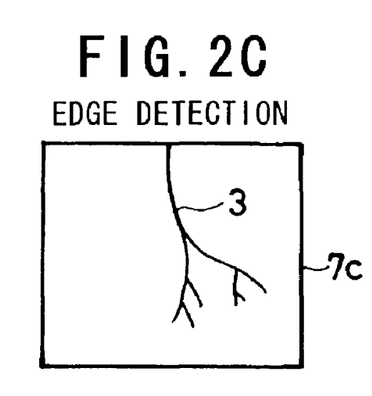
FIG. 2C is an edge-detected image and FIG. 2D shows an image after an addition.

The output of the above-described binarization circuit 20 is supplied to the edge detection circuit 22 where the area where the signal level changes slowly (low-frequency component) is removed and the area where the signal level changes drastically is thereby detected, and in this way the position signal of the blood vessel 3 shown in the image 7c in FIG. 2C is extracted. Then, the output of this edge detection circuit 22 is supplied to the gate of the three-state buffer 26.

The three-state buffer 26 extracts the $R_0$, $G_0$, and $B_0$ signals Making up the blood vessel image based on the blood vessel position signals detected by the above-described edge detection circuit 22 and the respective color signals of this blood vessel image are amplified at a predetermined amplification factor by amplifier 28. That is, if this amplification factor is assumed to be "a", the amplifier 28 outputs $R_1=aR_0$, $G_1=aG_0$ and $B_1=aB0$. Then, these signals $R_1$, $G_1$ and $B_1$ are added to $R_0$, $G_0$, and $B_0$, the signals of the original image by the adder 130.

Figure 2D:
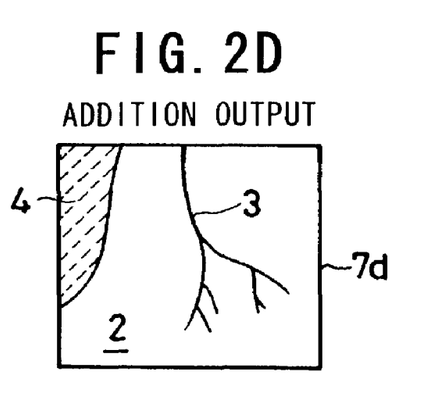

Therefore, the adder 30 outputs $R_2=(a+1)R_0$, $G_2=(a+1)G_0$, $B_2=(a+1)B_0$, and the object image 7d shown in FIG. 2D is displayed on the monitor via the signal processing circuit 32. This image 7d clearly displays the blood vessel (capillary blood vessel) 3 with ×(a+1) chroma in the mucous membrane 2 with high contrast, which consequently makes it possible to clearly observe the blood circulation state and concentration situation of the blood vessel 3, make a diagnosis of the focus and identify a cancerous tissue, etc. with reference to the blood circulation state, etc. of this blood vessel 3.

Second Embodiment

Figure 3:
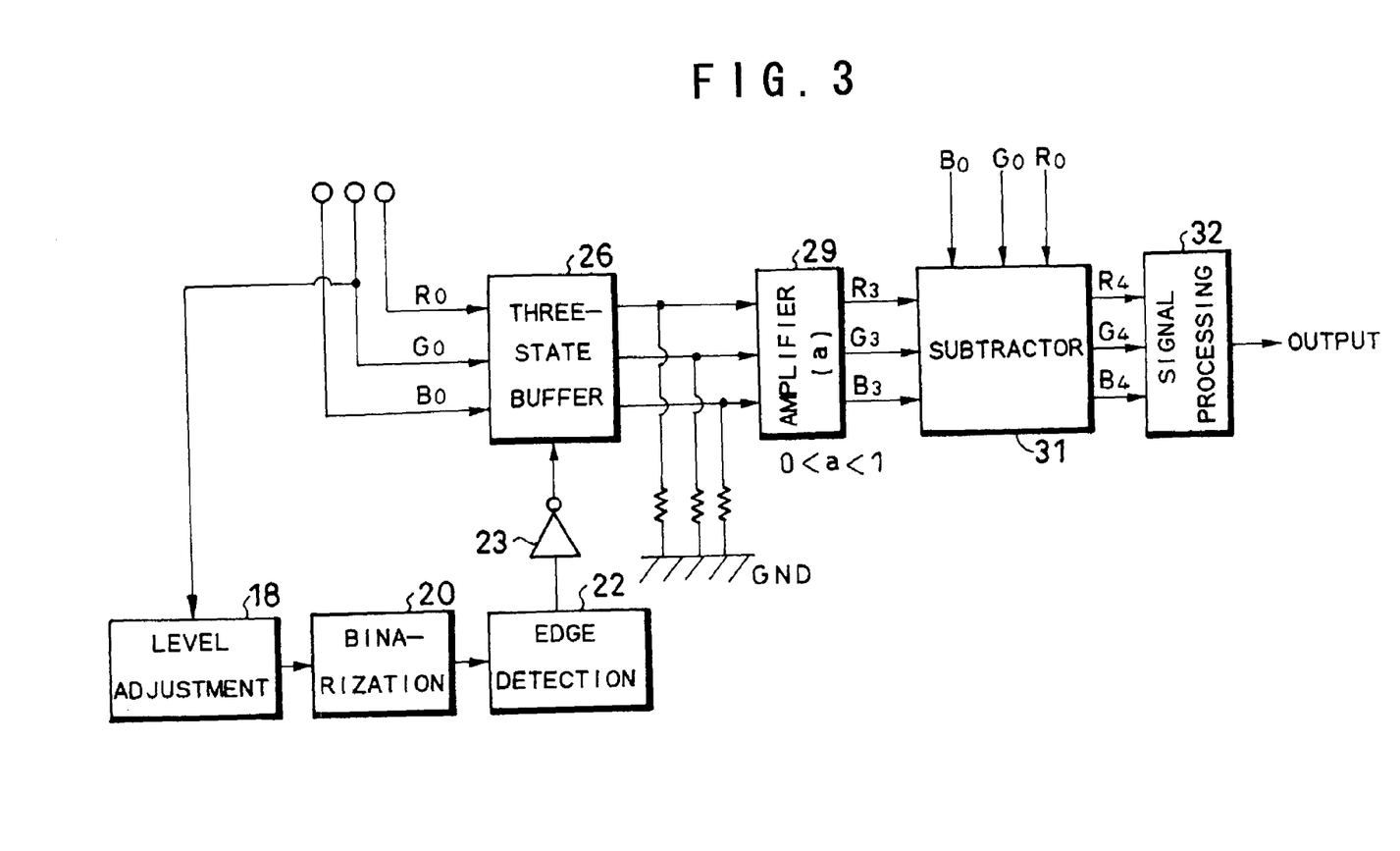
FIG. 3 is a block diagram showing a main configuration of a second embodiment.

FIG. 3 shows a configuration of a second embodiment of the present invention and this second embodiment reduces the chroma of images other than those of blood vessels. That is, as shown in FIG. 3, an inverter 23 is inserted between an edge detection circuit 22 and three-stage buffer 26, which inverts the output of the edge detection circuit 22 and supplies the inverted output to the three-state buffer 26. This three-state buffer 26 is followed by an amplifier 29 whose amplification factor "a" ranges from 0 to 1 and a subtractor 31.

According to this second embodiment, signals (position signals) of images other than those of blood vessels are extracted through an inversion operation of the inverter 23, and thus signals $R_0$, $G_0$ and $B_0$ making up images other than those of blood vessels are extracted from the three-state buffer 26 and the respective color signals are amplified at an amplification factor "a" (0<a<1) by the amplifier 29. That is, the amplifier 29 outputs $R_3=aR_0$, $G_3=aG_0$ and $B_3=aB_0$. Then, these color signals $R_3$, $G_3$ and $B_3$ are subtracted from $R_0$, $G_0$ and $B_0$, the signals of the original image by the subtractor 31.

Therefore, the subtractor 31 outputs $R_4=(1-a)R_0$, $G_4=(1-a)G_0$, $B_4=(1-a)B_0$, and the object image is displayed on the monitor through the signal processing circuit 32. This image clearly displays the blood vessel 3 in the mucous membrane 2 and dark area 4 having ×(1−a) chroma with high contrast, as in the case of the first embodiment.

Third Embodiment

Figure 4:
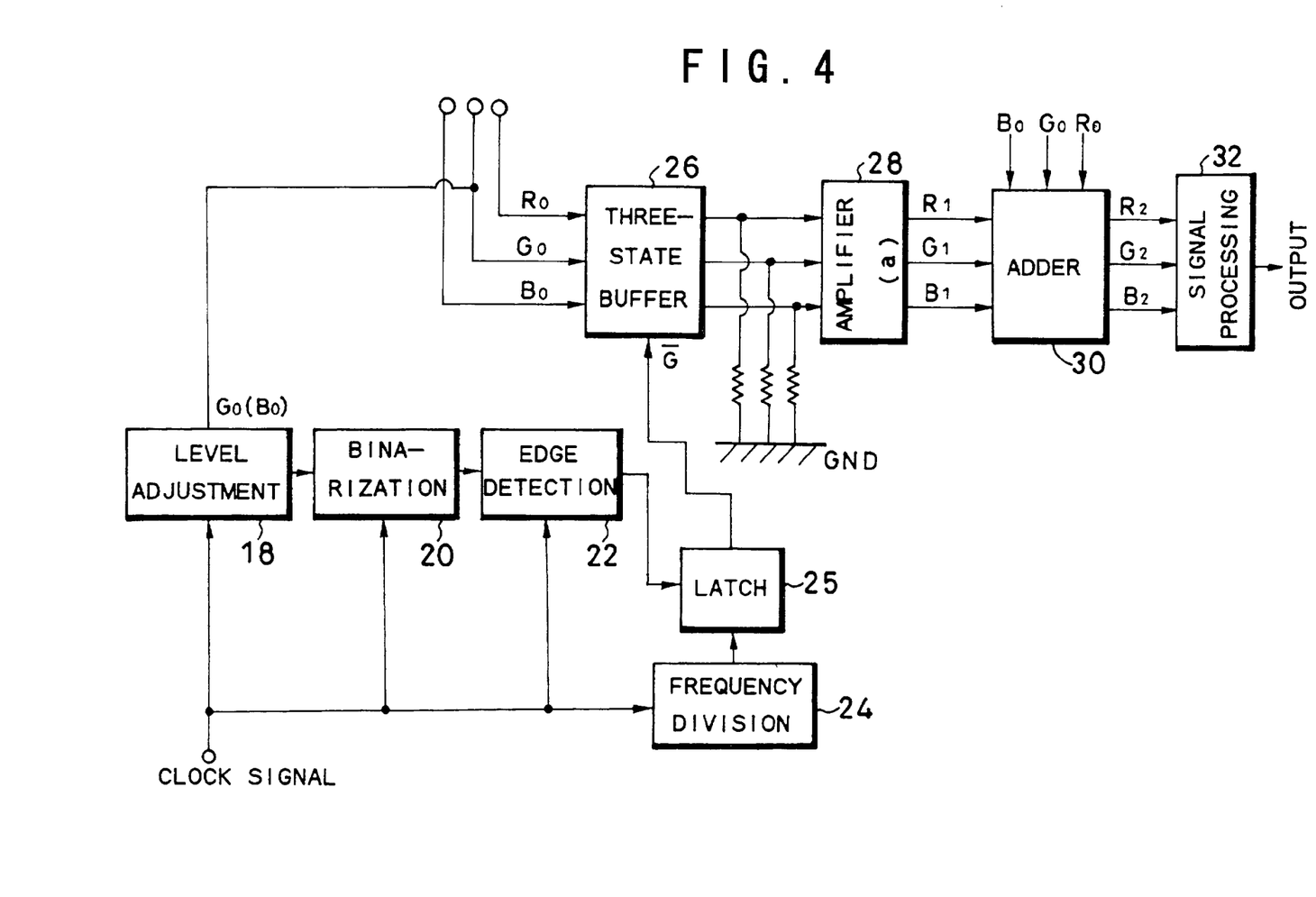
FIG. 4 is a block diagram showing a main configuration of a third embodiment.

FIG. 4 shows a configuration of a third embodiment of the present invention and this third embodiment displays thickened blood vessels. As shown in FIG. 4, in addition to the configuration of the first embodiment, the third embodiment provides a frequency division circuit 24 that divides a clock signal and generates a slower clock signal and a latch circuit 25 that latches $R_0$, $G_0$ and $B_0$ signals making up a blood vessel image using the outputs of this slow clock signal and the edge detection circuit 22. That is, the above-described frequency division circuit 24 divides the clock signal (frequency $f_1$) input by, for example, 2 and the above-described latch circuit 25 gives a latch signal for doubling the thickness of the blood vessel to the three-state buffer 26 through a clock signal with a double cycle (frequency ($f_1/2$)) and blood vessel signal.

As in the case of the first embodiment, according to this third embodiment, the $G_0$ signal output from the color conversion circuit 17 is amplified by the level adjusting circuit 18, converted to a binarized signal by the binarization circuit 20 and the edge detection circuit 22 extracts a blood vessel position signal based on this binarized signal. Then, the latch circuit 25 latches the blood vessel part of the $R_0$, $G_0$, and $B_0$ signals supplied to the three-state buffer 26 based on a slow clock signal with a double cycle and blood vessel position signal. In FIG. 4, the image adder 130 of FIG. 1 is shown as 30.

Figure 5A:
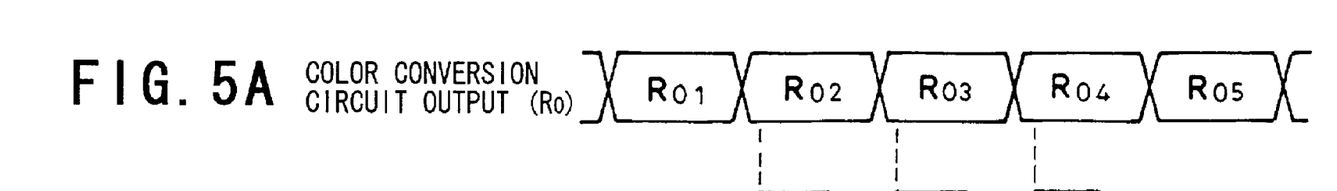
FIG. 5A to FIG. 5E illustrate latch processing of image data executed in the third embodiment.
Figure 5B:
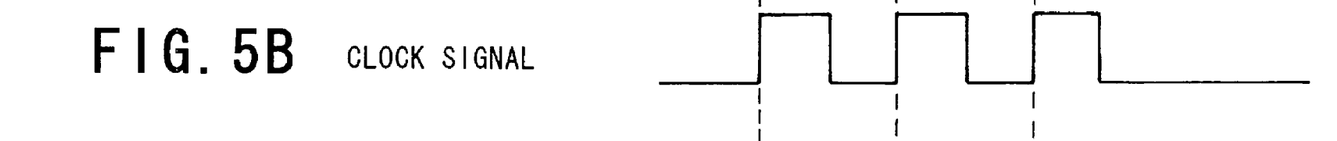
Figure 5C:
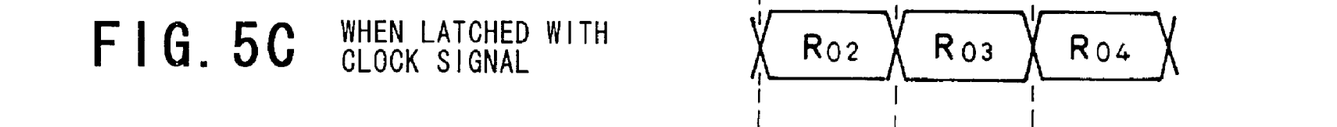
Figure 5D:
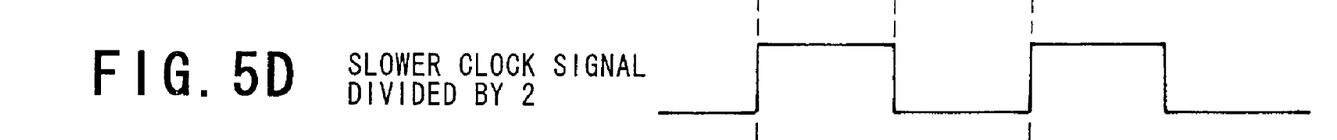
Figure 5E:
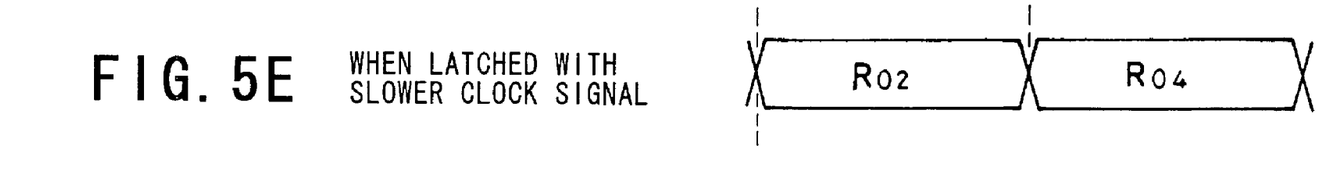

FIG. 5A to FIG. 5E show $R_0$ signals making up a blood vessel image obtained from this three-state buffer 26 (the same applies to $G_0$ and $B_0$), and when the blood vessel part is latched for the output data of the color conversion circuit 17 shown in FIG. 5A based on the image processing clock signal shown in FIG. 5B, signals $R_{02}$, $R_{03}$, $R_{04}$ are output in the same cycle as that in FIG. 5A as shown in FIG. 5C. In contrast, the third embodiment latches the blood vessel part based on a slow clock signal shown in FIG. 5D and outputs signals $R_{02}$ and $R_{04}$ with a cycle twice as long as a normal cycle as shown in FIG. 5E.

Thus, when the $R_0$, $G_0$ and $B_0$ signals making up an image of a double-thick blood vessel are extracted from the three-stage buffer 26, these signals are amplified by the amplifier 28 at an amplification factor "a" as in the case of the first embodiment and the $R_1$, $G_1$ and $B_1$ signals which are outputs of this amplifier 28 are added to the $R_0$, $G_0$ and $B_0$ signals of the original image by the adder 30.

Figure 6A:
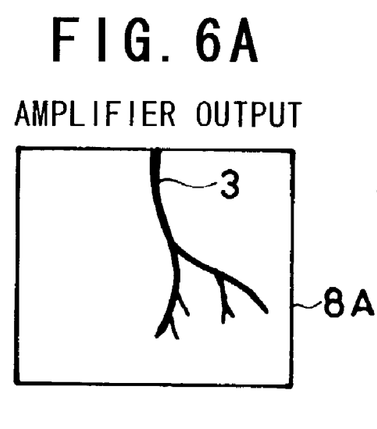
FIG. 6A and FIG. 6B show images formed by the respective circuits of the third embodiment.
Figure 6B:
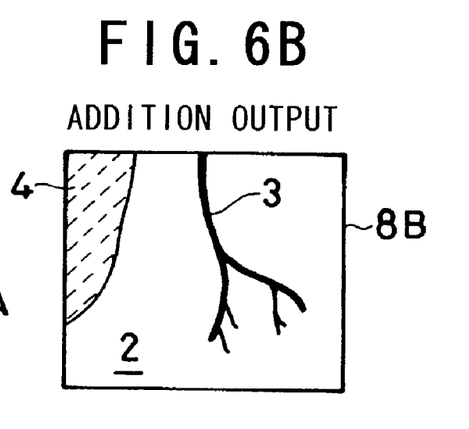

FIG. 6A and FIG. 6B show images formed in the above-described process, and as shown in FIG. 6A, the image 8A obtained by the above-described amplifier 28 shows the blood vessel 3 doubling in thickness. Furthermore, as shown in FIG. 6B, in the image 8B obtained by the adder 30, the blood vessel 3 doubling in thickness and with ×(1+a) chroma is displayed in the mucous membrane 2 accompanied by the dark area 4.

The aforementioned embodiments extract a blood vessel signal based on the G signal, but it is also possible to input the B signal to the level adjusting circuit 18 and extract a blood vessel position signal. That is, this embodiment detects the position of a blood vessel from an image signal with colors other than red, the principal color of the blood vessel and use color signals other than the R signal. Furthermore, in the above third embodiment, it is also possible to adopt the configuration of the second embodiment in which the chroma of images other than those of blood vessels is reduced.

As explained above, the first to third embodiments can clearly display blood vessels in high contrast to other tissue such as mucous membranes on the monitor and provide useful information for observation and diagnoses of an object. Furthermore, if the blood vessel position signal output from the edge detection circuit is re-detected with a clock signal slower than an image processing clock signal, it is possible to display thicker blood vessels and increase the recognition level of blood vessels in the object image.

Fourth Embodiment

Figure 7:
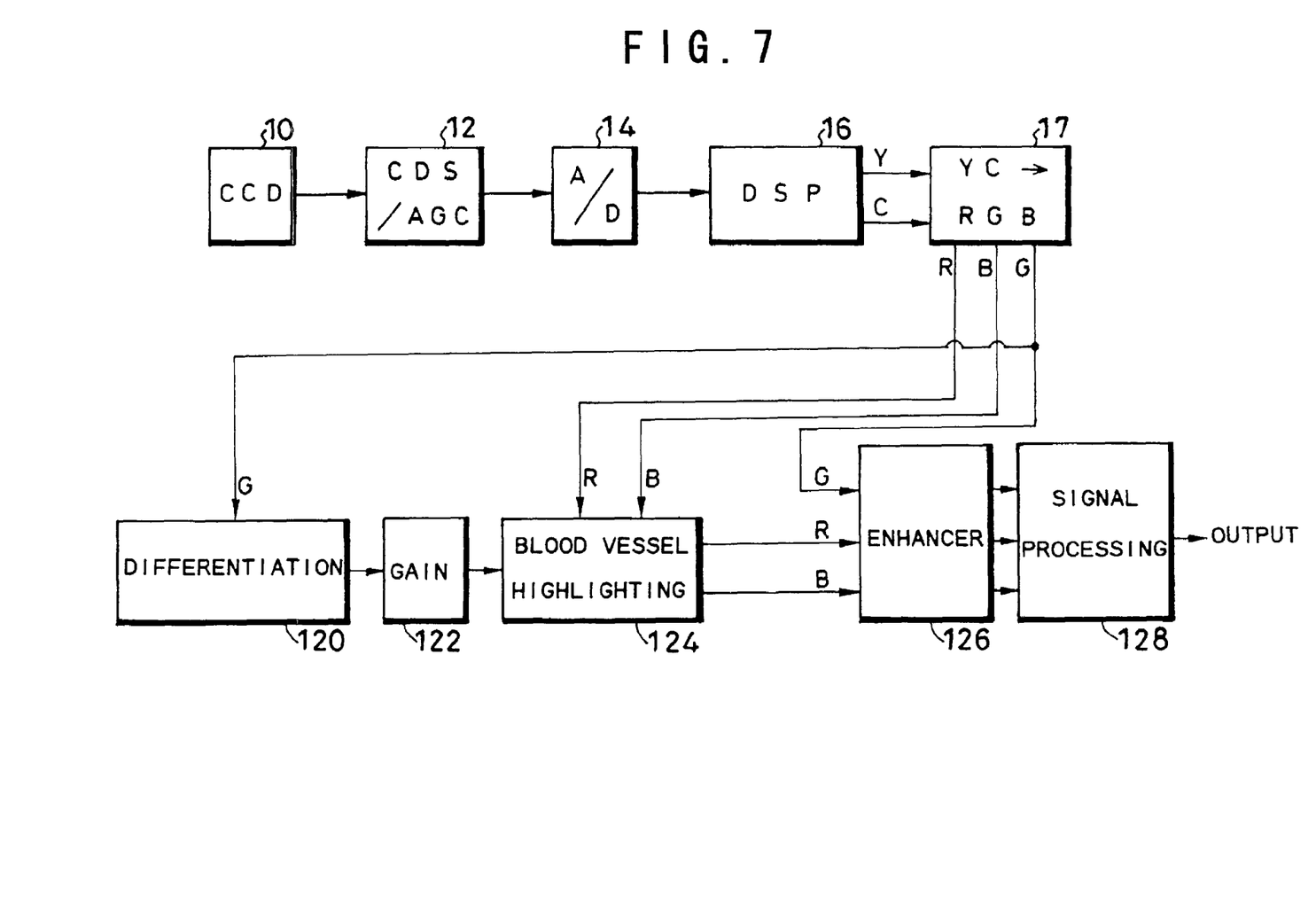
FIG. 7 is a block diagram showing a main configuration of an electronic endoscope according to a fourth embodiment of the present invention.

FIG. 7 shows a configuration of a fourth embodiment and as in the case of the first embodiment, this electronic endoscope is provided with a CCD 10, an A/D converter 14, a DSP 16 that forms a brightness (Y) signal and color difference (C) signals of R-Y and B-Y and a color conversion circuit 17 that converts these Y signal and C signal to R (red), G (green) and B (blue) signals. By the way, it is also possible to directly form RGB signals inside the DSP 16 and a power scaling lens is incorporated in the objective optical system.

Furthermore, this embodiment is also provided with a differentiating circuit 120 that differentiates a G signal input from the color conversion circuit 17 above, a gain circuit 122 that amplifies the differential signal output from this differentiating circuit 120 and a blood vessel highlighting circuit 124 that amplifies the R and B signals output from the conversion circuit 118 above by a differential signal obtained at this gain circuit 122 and these circuits perform processing of extracting blood vessels.

Figure 8A:
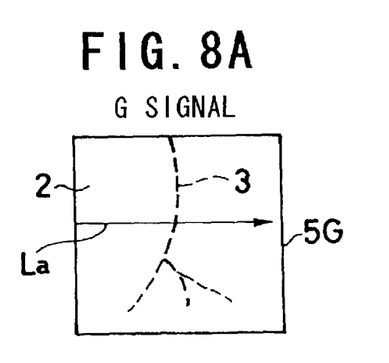
Figure 8B:
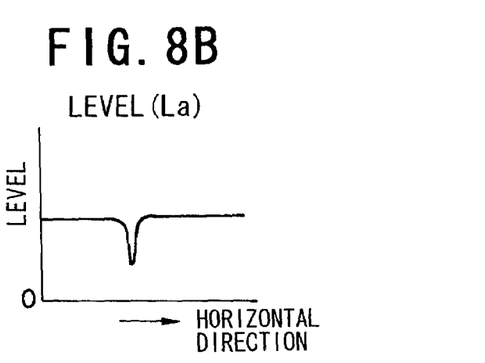
FIG. 8B shows a signal level of a horizontal line La of the G signal image in FIG. 8A

That is, FIG. 8A shows an image 5G by a G signal input to the differentiating circuit 120 and in this G image, the blood vessel 3 shown with dotted line is at a low level (level close to black). Here, the signal level of the horizontal line La of this G image 5 corresponds to a signal level which drops drastically in the area corresponding to the blood vessel 3 as shown in FIG. 8B. The differentiating circuit 120 differentiates this signal to form a differential signal showing a drastic change that drops, then rises by an amount doubling that of this drop and drops again to the initial level.

Figure 9A:
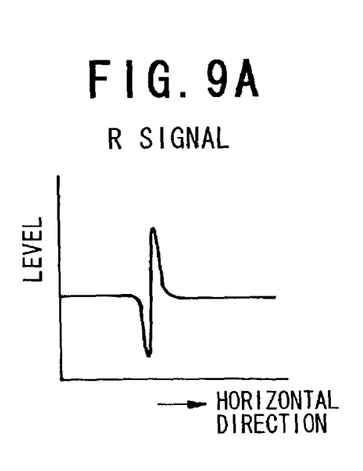
Figure 9B:
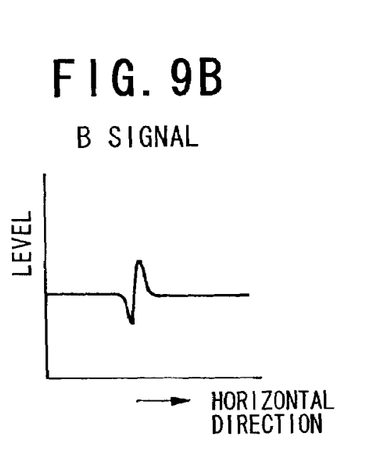

Then, the gain circuit 122 above amplifies the differential signal output from the differentiating circuit 120 at a predetermined amplification factor g to a signal with a larger level difference, and the blood vessel highlighting circuit 124 above amplifies the R signal and B signal using this differential signal as a gain signal and forms the R signal with a level difference for highlighting blood vessels as shown in FIG. 9A and the B signal in FIG. 9B.

The blood vessel highlighting circuit 124 is further followed by an enhancer 126 for entering the R and B signals to highlight the blood vessels above, entering the G signal output from the color conversion circuit 118 and enhancing the contour from these signals and this enhancer 126 is provided with a signal processing circuit 128 to apply various types of processing for monitor output.

The fourth embodiment has the above-described configuration and the DSP 16 forms a Y signal subjected to various types of image processing and C signals of R-Y and B-Y based on the output signal from the CCD 10, and this Y signal and C signal are converted to R, G and B color signals by the color conversion circuit 118.

Figure 8C:
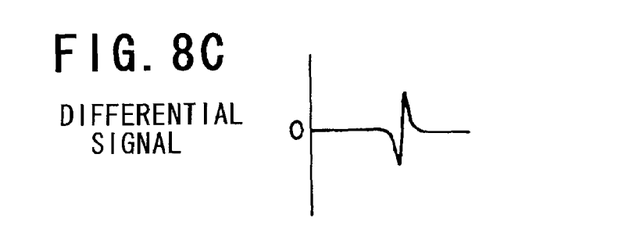
FIG. 8C shows a differential signal of the G signal in FIG. 8B.

The G signal of these signals is output to the enhancer 126, which is a contour highlighting circuit, and at the same time supplied to the differentiating circuit 120 and this differentiating circuit 120 obtains a differential signal shown in FIG. 8C corresponding to the blood vessel positions based on this G signal. This differential signal is amplified at a predetermined amplification factor g by the gain circuit 122 and supplied to the blood vessel highlighting circuit 124 as its gain signal. In this blood vessel highlighting circuit 124, the R signal and B signal are amplified by a differential signal as gain signals (or multiplied by a differential signal as a coefficient) and an R signal in FIG. 9A and a B signal in FIG. 9B with the blood vessel areas highlighted (these are shown as horizontal line La signals in FIG. 8A) are formed. Then, these R and B signals together with the G signal output from the color conversion circuit 118 are supplied to the enhancer 126, subjected to contour highlighting processing and then subjected to various types of processing for monitor output by the signal processing circuit 128.

Figure 10A:
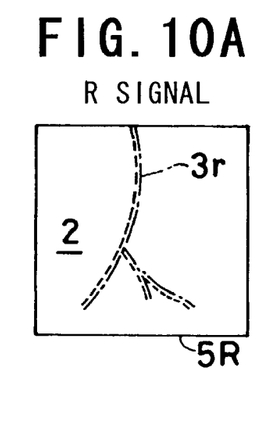
Figure 10B:
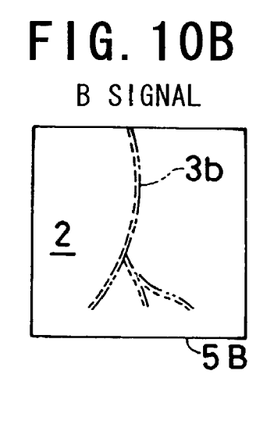
Figure 10C:
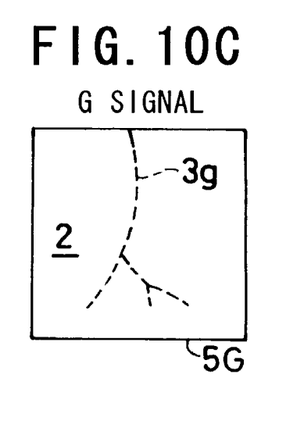
Figure 10D:
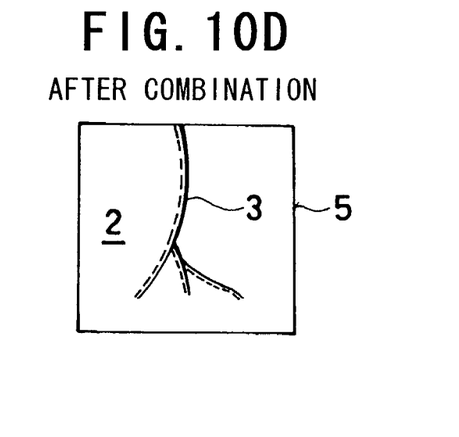

FIG. 10A to FIG. 10D illustrate color formation at the above-described blood vessel area and FIG. 10A shows an image 5R by the R signal (FIG. 9A) output from the above-described blood vessel highlighting circuit 124 and shows an image expressing blood vessels by a black dotted line area and red 1-dot dashed line area 3r (area composed of both lines running in parallel). FIG. 10B is an image 5B by the B signal (FIG. 9B) output from the above-described blood vessel highlighting circuit 24 and becomes an image expressing blood vessels by a black dotted line area and blue 2-dot dashed line area 3b in this case, too. Then, FIG. 10C is an image of the G signal output from the above-described color conversion circuit 118 and when these RGB signals are combined, as shown in FIG. 10D, the blood vessel 3 made up of the black dotted line area and the solid line RGB combined section is displayed.

Thus, finally, the monitor image clearly shows the blood vessel (capillary blood vessel) 3 in the mucous membrane 2 in sharp contrast and as a result, it is possible to clearly observe the blood circulation state and concentration situation of the blood vessel 3 and optimally make a diagnosis of focuses and identify cancerous tissue, etc. with reference to the blood circulation state, etc. of this blood vessel 3.

In the above fourth embodiment, the blood vessel highlighting circuit 124 amplifies the R signal and B signal based on a differential signal, but it is also possible to amplify only this R signal to highlight blood vessels. Furthermore, the above differentiating circuit 120 obtains a differential signal based on the G signal, but it is also possible to enter the B signal to generate a differential signal and execute the above-described blood vessel highlighting processing based thereon. That is, this embodiment detects the existence (position) of blood vessels from image signals with colors other than red color which is the principal color of blood vessels and can also use color signals other than the G signal.

As explained above, the fourth embodiment generates a differential signal obtained by differentiating the G signal other than the R signal which is the principal color signal of blood vessels, amplifies the signal, amplifies at least the R signal based on this differential signal to highlight blood vessels and can thereby clearly display blood vessels in high contrast to other tissue such as mucous membranes on the monitor.

Fifth Embodiment

Figure 11:
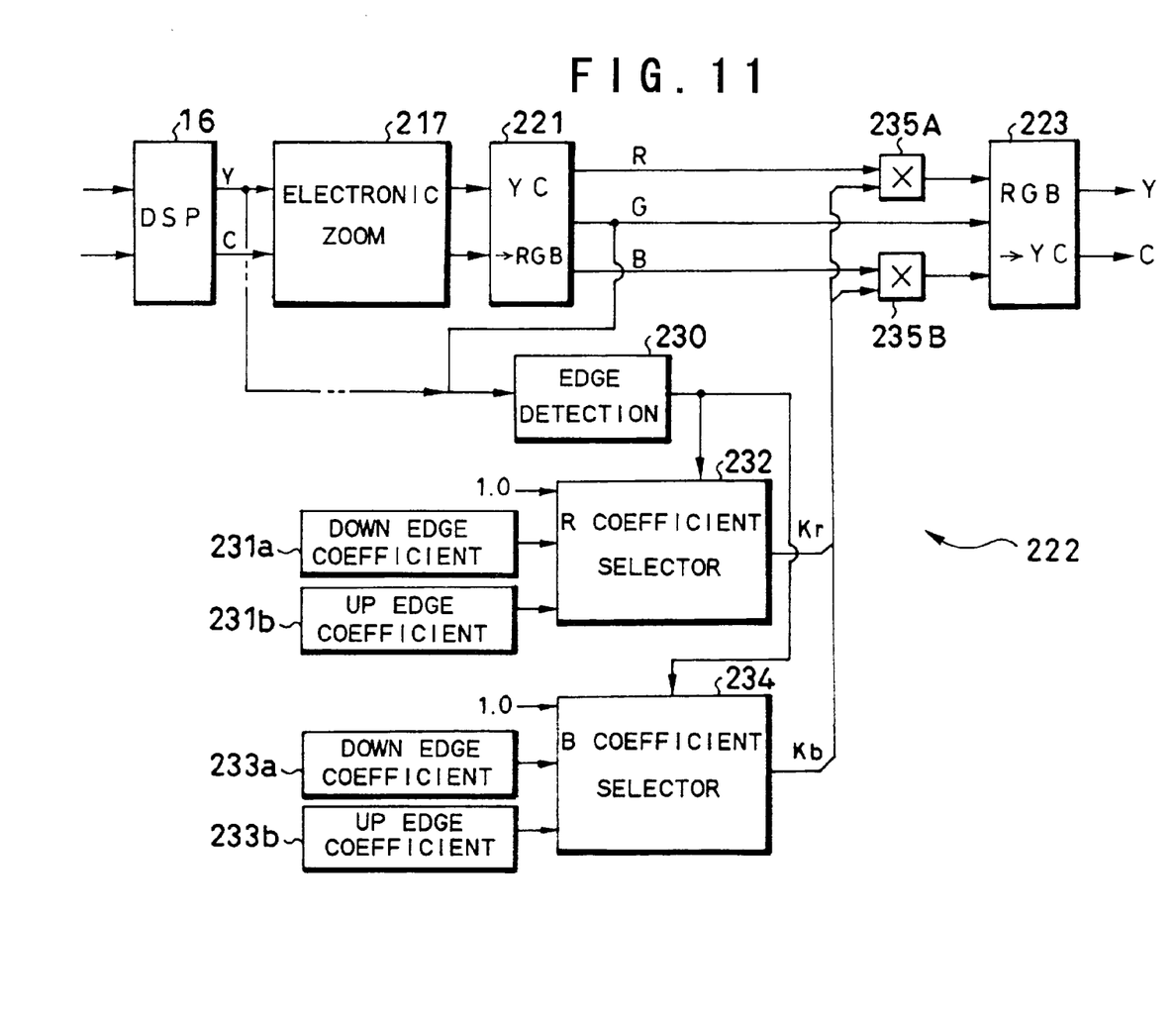
FIG. 11 is a block diagram showing a configuration related to blood vessel highlighting of an electronic endoscope according to a fifth embodiment of the present invention.

FIG. 11 shows a configuration related to highlighting of blood vessel by an electronic endoscope according to a fifth embodiment and the DSP 16 is followed by an electronic zoom circuit 217 that magnifies images based on a zoom switch and this electronic zoom circuit 217 is followed by an RGB color conversion circuit 221 that color-converts the Y signal and C signal to R (red), G (green) and B (blue) signals. This embodiment is provided with a blood vessel highlighting circuit 222 which is fed the signal of this RGB color conversion circuit 221 for clearly displaying blood vessels.

As this blood vessel highlighting circuit 222, there are an edge detection circuit 230 that detects a down edge section and an up edge section of blood vessels from the image of the G signal entered, coefficient generation circuits (or can also be memory, etc.) 231a and 231b that give a down edge coefficient and up edge coefficient Kr to the R signal, an R coefficient selector 232 that selects these coefficients (and 1) Kr, coefficient generation circuits 233a and 233b that give a down edge coefficient and up edge coefficient Kb to the B signal, a B coefficient selector 234 that selects these coefficients (and 1) Kb, multipliers 235A and 235B that multiply coefficients Kr and Kb. This blood vessel highlighting circuit 222 is followed by a YC color conversion circuit 223 that inversely converts the R, G and B signals to a Y signal and C signal.

Figure 12A:
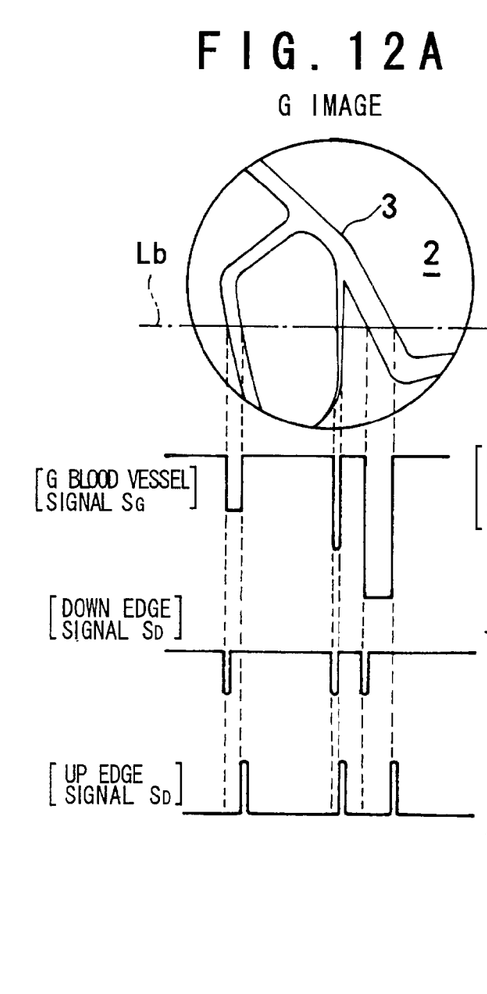
Figure 12B:
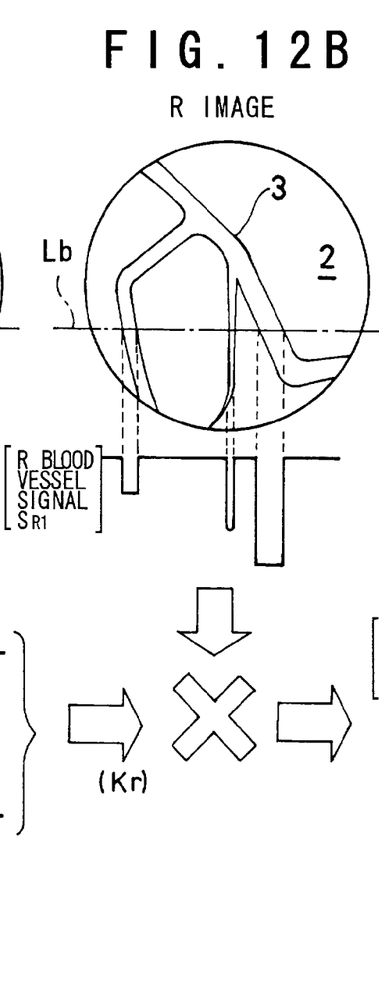
Figure 12C:
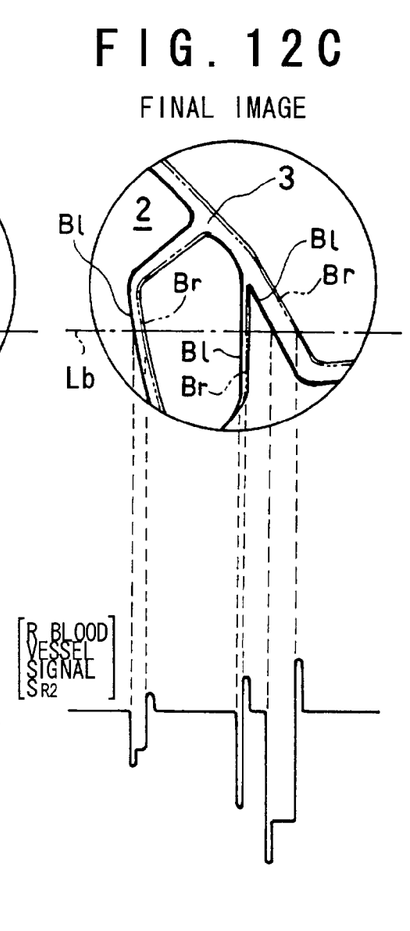

FIG. 12A to FIG. 12C show signal processing states of this blood vessel highlighting circuit 222 and assuming that a blood vessel signal $S_G$ is obtained on a line Lb of the G signal image as shown in FIG. 12A, the above-described edge detection circuit 230 detects the falling timing of this signal as a down edge signal $S_D$ indicating the down edge section and detects the rising timing of this signal as an up edge signal $S_u$ indicating the up edge section. Then, when the above-described down edge signal $S_D$ is detected, the R coefficient selector 232 selects, for example, 0.6 ($\leq 1$) as the coefficient Kr and when the above-described up edge signal $S_U$ is detected, the R coefficient selector 232 selects, for example, 1.6 ($\geq 1$) as the coefficient Kr and gives this to the multiplier 235A. Likewise, the B coefficient selector 234 also selects a predetermined coefficient Kb (the same coefficient as above or different coefficient from above) in association with the detected down edge signal $S_D$ and up edge signal $S_U$ and supplies these signals to the multiplier 235B.

For example, as shown in FIG. 12B, when a signal $S_{R1}$ of the blood vessel 3 is obtained on the line Lb of the R signal image, a blood vessel signal $S_{R2}$ in the figure is formed from this blood vessel signal $S_{R1}$ by multiplying the position signals specified by the above-described down edge signal $S_p$ and up edge signal $S_U$ by the coefficient Kr. That is, this signal $S_{R2}$ is a signal whose down edge section is further reduced and whose up edge section is further increased and highlighted and according to this blood vessel signal $S_{R2}$, the final image shows the blood vessel 3 with the blackish left end part B1 (thick line) of the blood vessel and the reddish right end part Br (2-dot dashed line) as shown in FIG. 12C.

The fifth embodiment has the configuration as shown above and the above-described blood vessel highlighting circuit 222 supplies a G signal to the edge detection circuit 230 and detects the down edge section and up edge section of the blood vessel 3 based on this G signal image. That is, as explained in FIG. 12A, the down edge signal $S_D$ and up edge signal $S_U$ of the G signal blood vessel are extracted and these signals $S_D$ and $S_U$ are supplied to the R coefficient selector 232 and B coefficient selector 234. Then, this R coefficient selector 232 selects a down edge coefficient of, for example, 0.6 for the down edge section and an up edge coefficient of, for example, 1.6 for the up edge section as the coefficient Kr and selects a coefficient of 1.0 for other areas. Then, this coefficient Kr is multiplied on the R signal by the multiplier 235A. As a result, as shown in FIG. 12C, an R blood vessel signal $S_{R2}$ is obtained where the down edge section is further reduced and the up edge section is increased.

On the other hand, the B coefficient selector 234 also selects a down edge coefficient of, for example, 0.8 for the down edge section and an up edge coefficient of, for example, 1.4 for the up edge section as the coefficient Kb and selects a coefficient of 1.0 for other areas. Then, this coefficient Kb is multiplied on the B signal by the multiplier 235B. As a result, a B blood vessel signal similar to $S_{R2}$ in FIG. 12C is obtained. Then, when the final image of this FIG. 3C is displayed on the monitor, both ends are highlighted with the left end part B1 in the blood vessel width direction expressed blackish and the right end section Br expressed reddish, thus clearly displaying the blood vessel 3 with optimal contrast.

What is claimed is:
1. An electronic endoscope comprising:
    a color signal formation circuit that forms predetermined color signals based on signals captured by an image pickup element;
    a binarization circuit that inputs color signals other than a red signal output from said color signal formation circuit and generates binarized image signals;

an edge detection circuit that inputs binarized signals output from said binarization circuit and detects blood vessel positions in an image;

a chroma correction circuit that adjusts chroma of the blood vessel image based on the blood vessel position signals output from said edge detection circuit and said color signals, wherein said color signal formation circuit forms red, green and blue color signals and said binarization circuit forms a binarized image by using the green signal or blue signal; and wherein said chroma correction circuit is designed to increase chroma of the blood vessel image.

2. The electronic endoscope according to claim 1, further comprising:

a blood vessel edge detection circuit that inputs predetermined signals output from said color signal formation circuit and detects both ends of the blood vessel in the width direction; and a multiplier that multiplies signals at both ends of the blood vessel detected by said blood vessel edge detection circuit by a predetermined coefficient to highlight the blood vessel.

3. An electronic endoscope comprising:

a color signal formation circuit that forms predetermined color signals based on signals captured by an image pickup element;

a binarization circuit that inputs color signals other than a red signal output from said color signal formation circuit and generates binarized image signals;

an edge detection circuit that inputs binarized signals output from said binarization circuit and detects blood vessel positions in an image;

a blood vessel redetection circuit that redetects the blood vessel position signals output from said edge detection circuit by a clock signal slower than the image processing clock signal; and a chroma correction circuit that adjusts chroma of the blood vessel image based on the blood vessel position signals output from said blood vessel redetection circuit and said color signals.

4. The electronic endoscope according to claim 3, wherein said chroma correction circuit is designed to increase chroma of the blood vessel image.

5. The electronic endoscope according to claim 3, further comprising a circuit for extracting signals other than the blood vessel position signals output from said blood vessel redetection circuit, wherein said chroma correction circuit is designed to decrease chroma of images other than the blood vessel image.

6. The electronic endoscope according to claim 3, further comprising:

a blood vessel edge detection circuit that inputs a predetermined signal output from said color signal formation circuit and detects both ends of the blood vessel in the width direction; and a multiplier that multiplies signals at both ends of the blood vessel detected by said blood vessel edge detection circuit by a predetermined coefficient to highlight the blood vessel.

7. An electronic endoscope comprising:

a color signal formation circuit that forms a predetermined color signal based on signals captured by an image pickup element;

a differentiating circuit that differentiates predetermined color signals other than a red color signal obtained at said color signal formation circuit and generates a differential signal;

a gain circuit that amplifies the differential signal output from said differentiating circuit;

a blood vessel highlighting circuit that amplifies at least a red signal other than said predetermined color signals based on the differential signal output from said gain circuit to highlight the blood vessel; and wherein said color signal formation circuit forms red, green and blue color signals, said differentiating circuit applies differential processing to the green signal; and said blood vessel highlighting circuit amplifies the red and blue signals by the differential signal.

8. The electronic endoscope according to claim 7, further comprising:

a blood vessel edge detection circuit that inputs predetermined signals output from said color signal formation circuit and detects both ends of the blood vessel in the width direction; and a multiplier that multiplies signals at both ends of the blood vessel detected by said blood vessel edge detection circuit by a predetermined coefficient to highlight the blood vessel.

9. An electronic endoscope comprising:

a color signal formation circuit that forms predetermined color signals based on signals captured by an image pickup element;

a binarization circuit that inputs color signals other than a red signal output from said color signal formation circuit and generates binarized image signals;

an edge detection circuit that inputs binarized signals output from said binarization circuit and detects blood vessel positions in an image;

a chroma correction circuit that adjusts chroma of the blood vessel image based on the blood vessel position signals output from said edge detection circuit and said color signals, wherein said color signal formation circuit forms red, green and blue color signals and said binarization circuit forms a binarized image by using the green signal or blue signal; and further comprising a circuit for extracting signals other than the blood vessel position signals output from said edge detection circuit, wherein said chroma correction circuit is designed to decrease chroma of images other than the blood vessel image.

* * * * *